(12) United States Patent
Isobe et al.

(10) Patent No.: US 8,834,579 B2
(45) Date of Patent: Sep. 16, 2014

(54) DYE COMPOSITION FOR HAIR DYEING AND METHOD FOR PRODUCING THE SAME

(71) Applicant: Hodogaya Chemical Co., Ltd., Tokyo (JP)

(72) Inventors: Masatoshi Isobe, Tokyo (JP); Kenichiro Suzuki, Tokyo (JP); Mitsuhiro Akiba, Tokyo (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/796,140

(22) Filed: Mar. 12, 2013

(65) Prior Publication Data

US 2013/0340182 A1   Dec. 26, 2013

Related U.S. Application Data

(60) Provisional application No. 61/663,212, filed on Jun. 22, 2012.

(51) Int. Cl.
| | |
|---|---|
| *A61Q 5/10* | (2006.01) |
| *C09B 44/02* | (2006.01) |
| *A61K 8/41* | (2006.01) |
| *A61Q 5/06* | (2006.01) |
| *A61K 8/43* | (2006.01) |

(52) U.S. Cl.
CPC ............... *A61K 8/411* (2013.01); *A61Q 5/065* (2013.01); *A61K 8/416* (2013.01); *A61K 8/43* (2013.01); *A61K 2800/432* (2013.01); *A61K 2800/43* (2013.01); *C09B 44/02* (2013.01); *A61Q 5/10* (2013.01)
USPC .................................... 8/405; 8/426; 534/615

(58) Field of Classification Search
CPC ......... A61Q 5/065; A61Q 5/10; A61K 8/416; A61K 2800/432
USPC ........................ 8/405, 426, 466, 547; 534/615
See application file for complete search history.

(56) References Cited

U.S. PATENT DOCUMENTS

| 3,524,842 | A | * | 8/1970 | Grossmann et al. | ........... 534/613 |
| 5,422,031 | A | * | 6/1995 | Nomura et al. | ................... 8/431 |
| 2004/0168264 | A1 | * | 9/2004 | Frick et al. | ........................ 8/405 |
| 2006/0162097 | A1 | | 7/2006 | Schmenger et al. | |
| 2008/0094549 | A1 | | 4/2008 | Sadamitsu | |
| 2010/0226008 | A1 | | 9/2010 | Higeta et al. | |

FOREIGN PATENT DOCUMENTS

| JP | 10-053970 A | 2/1998 |
| JP | 11-124510 A | 5/1999 |
| JP | 2007-508253 A | 4/2007 |
| JP | 2008-050418 A | 3/2008 |
| JP | 2010-195909 A | 9/2010 |
| WO | WO-2006/057214 A1 | 6/2006 |
| WO | WO-2009/057676 A1 | 5/2009 |

OTHER PUBLICATIONS

STIC Search Report dated Jan. 8, 2014.*
SCCP (Scientific Committee on Consumer Products), Opinion on Basic Brown 16, Sep. 30, 2008, pp. 1-24.
International Search Report dated Jun. 25, 2013, issued for PCT/JP2013/003339.

* cited by examiner

*Primary Examiner* — Eisa Elhilo
(74) *Attorney, Agent, or Firm* — Edwards Wildman Palmer LLP

(57) ABSTRACT

The present invention relates to an azo dye composition for hair dyeing that has an excellent performance as a dye for hair dyeing and proves negative in the Ames test, and also relates to a method for producing the composition. An object of the present invention is to develop a purification method for a dye composition for hair dyeing mainly containing an azo dye and proving negative in the Ames test, and to provide the dye composition for hair dyeing that is produced by applying the purification method and indicates negative in the Ames test. The dye composition for hair dyeing contains, as a main component, the azo dye having trimethylammonio, and the dye composition for hair dyeing is characterized in that the result of the Ames test is negative.

12 Claims, No Drawings

DYE COMPOSITION FOR HAIR DYEING AND METHOD FOR PRODUCING THE SAME

CROSS-REFERENCE TO RELATED APPLICATIONS

The present application claims priority to U.S. provisional application 61/663,212, filed Jun. 22, 2012, the entire description of which is herein incorporated by reference especially as disclosure.

BACKGROUND OF THE INVENTION

1. Field of the Invention

The present invention relates to an azo dye composition for hair dyeing that has an excellent performance as a dye for hair dyeing and proves negative in the Ames test, and also relates to a method for producing the composition.

2. Description of the Related Art

In recent years, there has been an increasing interest in the safety of chemical substances. Measures of strict legal regulation are taken particularly against production and sale of a carcinogenic substance, and it is mandatorily required to confirm that there is no carcinogenicity when developing a novel chemical substance. Although a long period and a huge cost are required for a test to determine the presence of carcinogenicity in a substance, a mutagenicity test is carried out as a test to determine in a short period and at a low cost the presence of carcinogenicity in a chemical substance. Particularly, the Ames test is broadly carried out as a method for allowing an effective screening of carcinogenicity of a chemical substance in a very simple detecting principle.

Basic Brown 16 represented by the following structural formula (I) is a useful azo dye having an excellent performance as a dye for hair dyeing. However, Basic Brown 16 is known to indicate positive in the Ames test (refer to, for example, Scientific Committee on Consumer Products. "Opinion on Basic Brown 16." Sep. 30, 2008), and a safety problem still remains in its practical application.

[Chemical Formula 1]

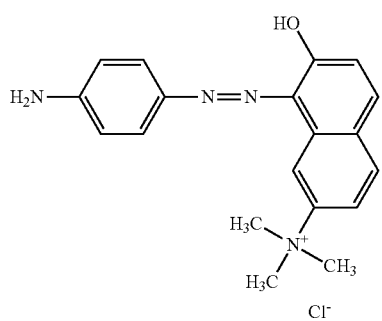

(I)

On the other hand, with respect to the anthraquinone dye represented by the following general formula (II), there is a known method for obtaining a dye that proves negative in the Ames test by performing a purification operation with column chromatography (refer to, for example, Japanese Unexamined Patent Application Publication No. 11-124510).

[Chemical Formula 2]

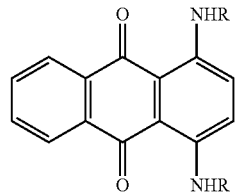

(II)

In the formula, R represents substituted or unsubstituted alkyl, alkenyl, or phenyl.

However, the purification method described in Japanese Unexamined Patent Application Publication No. 11-124510, which can be applied in the case of the anthraquinone dye, cannot be applied to dyes such as an azo dye (refer to, for example, Japanese Unexamined Patent Application Publication No. 11-124510).

The contents of Japanese Unexamined Patent Application Publication No. 11-124510, Scientific Committee on Consumer Products. "Opinion on Basic Brown 16." Sep. 30, 2008, Hosoda, Yutaka. Riron Seizo Senryo Kagaku, fifth edition, GIHODO SHUPPAN Co., Ltd., 1968, and "Bacterial Reverse Mutation Test." OECD GUIDELINE FOR TESTING OF CHEMICALS, no. 471, Adopted: 21, Jul. 1997 are incorporated herein by reference in their entirety.

SUMMARY OF THE INVENTION

Problems to be Solved by the Invention

An object of the present invention is to develop a purification method for a dye composition for hair dyeing containing an azo dye as a main component and proving negative in the Ames test, and to provide the dye composition for hair dyeing that is produced by applying the purification method and indicates negative in the Ames test.

Means of Solving the Problems

As a result of a thorough analysis made by the present inventors in order to achieve the foregoing objects, the present invention was completed by specifying impurities that indicate positive in the Ames test among impurities in the azo dye contained in the dye composition for hair dyeing containing the azo dye as a main component, by analyzing a variety of purification methods for the purpose of removing the impurities, and by carrying out the purification by a specific method to find that the dye composition for hair dyeing containing the azo dye as a main component indicates negative in the Ames test. That is, a summary of the present invention is as follows.

In a first aspect of the present invention, the dye composition for hair dyeing contains, as a main component, an azo dye having trimethylammonio, and the dye composition for hair dyeing is characterized in that the result of the Ames test is negative.

In a second aspect of the present invention, the dye composition for hair dyeing described in the above first aspect of the present invention is characterized in that the azo dye having trimethylammonio is represented by the following general formula (1).

[Chemical Formula 3]

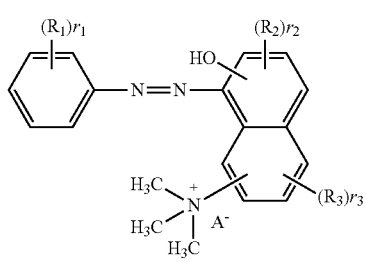

(1)

In the formula, $R_1$ to $R_3$ may be the same or different, and represent a hydrogen atom, nitro, amino, linear or branched alkyl of 1 to 10 carbon atoms that may have a substituent, cycloalkyl of 3 to 10 carbon atoms that may have a substituent, linear or branched alkyloxy of 1 to 10 carbon atoms that may have a substituent, cycloalkyloxy of 3 to 10 carbon atoms that may have a substituent, or a substituted or unsubstituted heterocyclic group. $r_1$ is an integer of 0 to 5, $r_2$ is an integer of 0 to 2, and $r_3$ is an integer of 0 to 3. $A^-$ represents an anion.

In a third aspect of the present invention, the dye composition for hair dyeing described in the above first aspect of the present invention is characterized in that the result of the Ames test is negative in the case of using *Salmonella typhimurium* TA98 strain and/or *Salmonella typhimurium* TA1537 strain in the test.

In a fourth aspect of the present invention, the dye composition for hair dyeing described in the above first aspect of the present invention is characterized in that the result of the Ames test is negative in the case of using *Escherichia coli* WP2 uvrA strain in the test.

In a fifth aspect of the present invention, the dye composition for hair dyeing described in the above first aspect of the present invention is characterized in that the content of the compound contained in the dye composition for hair dyeing and represented by the following general formula (2) is 0.3 wt. % or less.

[Chemical Formula 4]

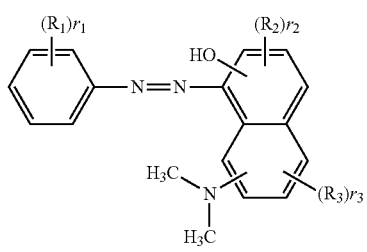

(2)

In the formula, $R_1$ to $R_3$ may be the same or different, and represent a hydrogen atom, nitro, amino, linear or branched alkyl of 1 to 10 carbon atoms that may have a substituent, cycloalkyl of 3 to 10 carbon atoms that may have a substituent, linear or branched alkyloxy of 1 to 10 carbon atoms that may have a substituent, cycloalkyloxy of 3 to 10 carbon atoms that may have a substituent, or a substituted or unsubstituted heterocyclic group. $r_1$ is an integer of 0 to 5, $r_2$ is an integer of 0 to 2, and $r_3$ is an integer of 0 to 3.

In a sixth aspect of the present invention, the dye composition for hair dyeing described in the above first aspect of the present invention is characterized in that the azo dye having trimethylammonio is Basic Brown 16 represented by the following structural formula (I).

[Chemical Formula 5]

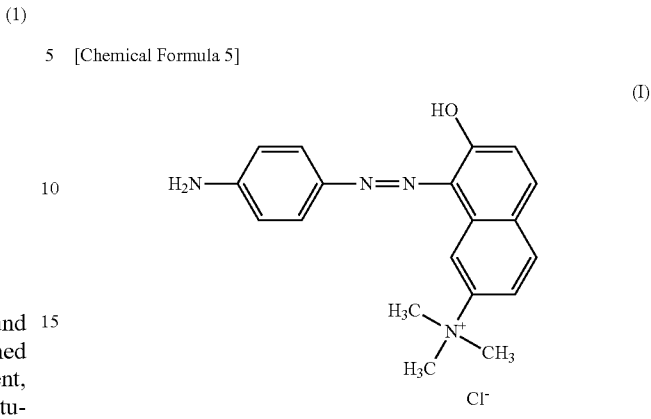

(I)

In a seventh aspect of the present invention, a purification method for the dye composition for hair dyeing containing, as a main component, the azo dye having trimethylammonio, is characterized in that the result of the Ames test in the dye composition for hair dyeing is negative.

In an eighth aspect of the present invention, the purification method for the dye composition for hair dyeing containing, as a main component, the azo dye having trimethylammonio, which is described in the above seventh aspect of the present invention, is characterized in that the purification is performed using activated carbon in a mixed solution of water and a water-soluble organic solvent.

In a ninth aspect of the present invention, the purification method described in the above seventh aspect of the present invention is characterized in that the azo dye having trimethylammonio is represented by the following general formula (1).

[Chemical Formula 6]

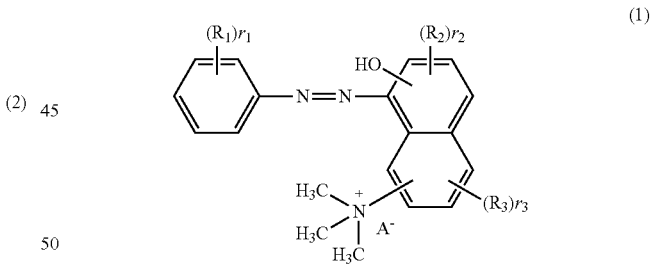

(1)

In the formula, $R_1$ to $R_3$ may be the same or different, and represent a hydrogen atom, nitro, amino, linear or branched alkyl of 1 to 10 carbon atoms that may have a substituent, cycloalkyl of 3 to 10 carbon atoms that may have a substituent, linear or branched alkyloxy of 1 to 10 carbon atoms that may have a substituent, cycloalkyloxy of 3 to 10 carbon atoms that may have a substituent, or a substituted or unsubstituted heterocyclic group. $r_1$ is an integer of 0 to 5, $r_2$ is an integer of 0 to 2, and $r_3$ is an integer of 0 to 3. $A^-$ represents an anion.

In a tenth aspect of the present invention, the purification method described in the above seventh aspect of the present invention is characterized in that the result of the Ames test is negative in the case of using *Salmonella typhimurium* TA98 strain and/or *Salmonella typhimurium* TA1537 strain in the test.

In an eleventh aspect of the present invention, the purification method described in the above eighth aspect of the present invention is characterized in that a water-soluble organic solvent is one or more selected from aliphatic alcohols and aliphatic ketones.

In a twelfth aspect of the present invention, the purification method described in the above seventh aspect of the present invention is characterized in that the content of the compound contained in the dye composition for hair dyeing and represented by the following general formula (2) is removed to 0.3 wt. % or less.

[Chemical Formula 7]

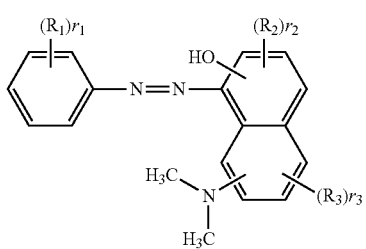

(2)

In the formula, $R_1$ to $R_3$ may be the same or different, and represent a hydrogen atom, nitro, amino, linear or branched alkyl of 1 to 10 carbon atoms that may have a substituent, cycloalkyl of 3 to 10 carbon atoms that may have a substituent, linear or branched alkyloxy of 1 to 10 carbon atoms that may have a substituent, cycloalkyloxy of 3 to 10 carbon atoms that may have a substituent, or a substituted or unsubstituted heterocyclic group. $r_1$ is an integer of 0 to 5, $r_2$ is an integer of 0 to 2, and $r_3$ is an integer of 0 to 3.

In a thirteenth aspect of the present invention, the purification method described in the above seventh aspect of the present invention is characterized in that the azo dye having trimethylammonio is Basic Brown 16 represented by the following structural formula (I).

[Chemical Formula 8]

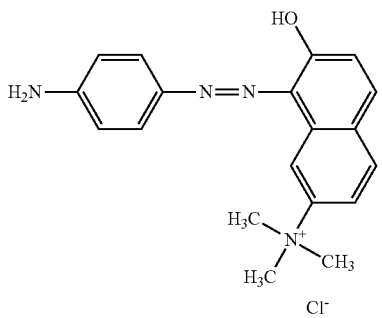

(I)

In a fourteenth aspect of the present invention, a producing method of the dye composition for hair dyeing containing, as a main component, the azo dye having trimethylammonio, is characterized in that the result of the Ames test in the dye composition for hair dyeing is negative.

Specific examples of the "linear or branched alkyl of 1 to 10 carbon atoms" or the "cycloalkyl of 3 to 10 carbon atoms" in the "linear or branched alkyl of 1 to 10 carbon atoms that may have a substituent" or the "cycloalkyl of 3 to 10 carbon atoms that may have a substituent" represented by $R_1$ to $R_3$ in the general formulae (1) and (2) include methyl, ethyl, n-propyl, isopropyl, n-butyl, isobutyl, tert-butyl, n-pentyl, isopentyl, neopentyl, n-hexyl, n-heptyl, isoheptyl, n-octyl, isooctyl, n-nonyl, isononyl, n-decyl, isodecyl, cyclopropyl, cyclopentyl, cyclohexyl, 1-adamantyl, and 2-adamantyl.

Specific examples of the "substituent" in the "linear or branched alkyl of 1 to 10 carbon atoms that has a substituent" or the "cycloalkyl of 3 to 10 carbon atoms that has a substituent" represented by $R_1$ to $R_3$ in the general formulae (1) and (2) can be a deuterium atom; trifluoromethyl; cyano; nitro; hydroxyl; halogen atoms such as a fluorine atom, a chlorine atom, a bromine atom, and an iodine atom; linear or branched alkyls of 1 to 10 carbon atoms such as methyl, ethyl, n-propyl, isopropyl, n-butyl, isobutyl, tert-butyl, n-pentyl, isopentyl, neopentyl, n-hexyl, n-heptyl, isoheptyl, n-octyl, isooctyl, n-nonyl, isononyl, n-decyl, and isodecyl; linear or branched alkoxys of 1 to 10 carbon atoms such as methyloxy, ethyloxy, and propyloxy; alkenyls such as allyl; aralkyls such as benzyl, naphthylmethyl, and phenethyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; heterocyclic groups such as pyridyl, furanyl, pyranyl, thienyl, furyl, pyrrolyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino, dithienylamino, and dipiperidinylamino, substituted with heterocyclic groups; dialkenylamino groups such as diallylamino; and disubstituted amino groups substituted with a substituent selected from alkyl, an aromatic hydrocarbon group, a condensed polycyclic aromatic group, aralkyl, a heterocyclic group, and alkenyl. These substituents may be further substituted with other substituents.

Specific examples of the "linear or branched alkyloxy of 1 to 10 carbon atoms" or the "cycloalkyloxy of 3 to 10 carbon atoms" in the "linear or branched alkyloxy of 1 to 10 carbon atoms that may have a substituent" or the "cycloalkyloxy of 3 to 10 carbon atoms that may have a substituent" represented by $R_1$ to $R_3$ in the general formulae (1) and (2) can be methyloxy, ethyloxy, n-propyloxy, isopropyloxy, n-butyloxy, tert-butyloxy, n-pentyloxy, n-hexyloxy, n-heptyloxy, isoheptyloxy, n-octyloxy, isooctyloxy, n-nonyloxy, isononyloxy, n-decyloxy, isodecyloxy, cyclopropyloxy, cyclopentyloxy, cyclohexyloxy, cycloheptyloxy, cyclooctyloxy, 1-adamantyloxy, and 2-adamantyloxy.

Specific examples of the "substituent" in the "linear or branched alkyloxy of 1 to 10 carbon atoms that has a substituent" or the "cycloalkyloxy of 3 to 10 carbon atoms that has a substituent" represented by $R_1$ to $R_3$ in the general formulae (1) and (2) can be a deuterium atom; trifluoromethyl; cyano; nitro; hydroxyl; halogen atoms such as a fluorine atom, a chlorine atom, a bromine atom, and an iodine atom; linear or branched alkyls of 1 to 10 carbon atoms such as methyl, ethyl, n-propyl, isopropyl, n-butyl, isobutyl, tert-butyl, n-pentyl, isopentyl, neopentyl, n-hexyl, n-heptyl, isoheptyl, n-octyl, isooctyl, n-nonyl, isononyl, n-decyl, and isodecyl; linear or branched alkoxys of 1 to 10 carbon atoms such as methyloxy, ethyloxy, and propyloxy; alkenyls such as allyl; aralkyls such as benzyl, naphthylmethyl, and phenethyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; heterocyclic groups such as pyridyl, furanyl, pyranyl, thienyl, furyl, pyrrolyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino, dithienylamino, and dipiperidinylamino, substituted with heterocyclic groups; dialkenylamino groups such as diallylamino; and disubstituted amino groups substituted with a substituent selected from alkyl, an aromatic hydrocarbon group, a condensed polycyclic aromatic group, aralkyl, a heterocyclic group, and alkenyl. These substituents may be further substituted with other substituents.

Specific examples of the "heterocyclic group" in the "substituted or unsubstituted heterocyclic group" represented by $R_1$ to $R_3$ in the general formulae (1) and (2) include pyridyl, furanyl, pyranyl, thienyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl.

Specific examples of the "substituent" in the "substituted heterocyclic group" represented by $R_1$ to $R_3$ in the general formulae (1) and (2) can be a deuterium atom; trifluoromethyl; cyano; nitro; hydroxyl; halogen atoms such as a fluorine atom, a chlorine atom, a bromine atom, and an iodine atom; linear or branched alkyls of 1 to 10 carbon atoms such as methyl, ethyl, n-propyl, isopropyl, n-butyl, isobutyl, tert-butyl, n-pentyl, isopentyl, neopentyl, n-hexyl, n-heptyl, isoheptyl, n-octyl, isooctyl, n-nonyl, isononyl, n-decyl, and isodecyl; linear or branched alkoxys of 1 to 10 carbon atoms such as methyloxy, ethyloxy, and propyloxy; alkenyls such as allyl; aralkyls such as benzyl, naphthylmethyl, and phenethyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; heterocyclic groups such as pyridyl, furanyl, pyranyl, thienyl, furyl, pyrrolyl, pyrrolidinyl, imidazolyl, imidazolinyl, imidazolidinyl, pyrazolyl, pyrazolinyl, pyrazolidinyl, pyridazinyl, pyrazinyl, piperidinyl, piperazinyl, thiolanyl, thianyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino, dithienylamino, and dipiperidinylamino, substituted with heterocyclic groups; dialkenylamino groups such as diallylamino; and disubstituted amino groups substituted with a substituent selected from alkyl, an aromatic hydrocarbon group, a condensed polycyclic aromatic group, aralkyl, a heterocyclic group, and alkenyl. These substituents may be further substituted with other substituents.

Specific examples of the "anion" represented by $A^-$ in the general formula (1) include halide ions such as a fluorine ion, a chlorine ion, a bromine ion, and an iodine ion; a sulfonate ion; alkylsulfate ions such as a methylsulfate ion; and a perchlorate ion.

Effects of the Invention

According to an embodiment of the present invention, a dye composition for hair dyeing containing, as a main component, an azo dye indicating negative in the result of the Ames test and having high safety, can be provided by carrying out a simple purification operation for the purpose of removing specific impurities without requiring a complicated operation.

DESCRIPTION OF THE EMBODIMENTS

The azo dye having trimethylammonio, which is used in the present invention, can be produced by a known method (refer to, for example, Hosoda, Yutaka. *Riron Seizo Senryo Kagaku*, fifth edition, GIHODO SHUPPAN Co., Ltd., 1968).

The following presents compounds as the azo dye having trimethylammonio, which is used in the present invention. The present invention, however, is not restricted to these compounds.

[Chemical Formula 9]

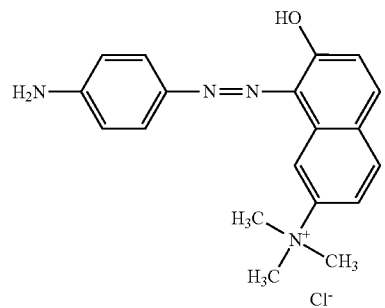

[Chemical Formula 10]

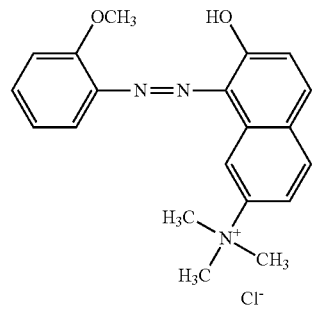

[Chemical Formula 11]

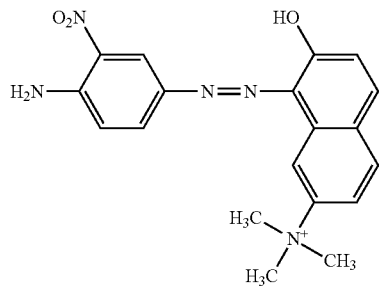

[Chemical Formula 12]

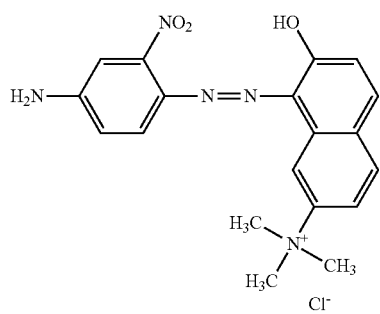

The Ames test is a test system for detecting a phenomenon that a histidine-requiring strain, which cannot grow without a specific amino acid (for example, histidine), is returned to a histidine-nonrequiring strain by a gene mutation due to a mutational substance. The Ames test is also called a reverse mutation test because a strain regains its original nature by a gene mutation. In the case of a metabolic activation test, a test substance, a test strain, and an enzyme for activating metabolism of drugs (S-9Mix) are mixed, and the mixture is cultured for 48 hours at 37° C. using an agar medium after preincubation for 20 minutes at 37° C. The number of induced revertant colonies is counted, and it is determined to be positive in the case where the ratio (MR value) of the number of the induced revertant colonies to the number of revertant colonies appearing in a negative control is 2 or more (refer to, for example, "Bacterial Reverse Mutation Test." *OECD GUIDELINE FOR TESTING OF CHEMICALS*, no. 471, Adopted: 21, Jul. 1997).

The metabolic activation test is a test carried out by adding an enzyme for activating metabolism of drugs (that is, S-9Mix) which is obtained from a liver of a rat or the like in order to bring a metabolic system of drugs for microbes close to that of mammals.

Among the strains, *Salmonella typhimurium* (TA1535 strain, TA1537 strain, TA100 strain, and TA98 strain) or *Escherichia coli* (WP2 uvrA strain) is generally used at present.

Basic Brown 16 represented by the structural formula (I) is known to indicate positive in the Ames test using TA1537 strain and/or TA98 strain among the strains (refer to Scientific Committee on Consumer Products. "Opinion on Basic Brown 16." Sep. 30, 2008).

Among impurities contained in Basic Brown 16, a component represented by the following structural formula (III), which indicates positive in the Ames test (especially, TA1537 strain and/or TA98 strain), was confirmed when separation and purification of components indicating positive in the Ames test were performed.

[Chemical Formula 13]

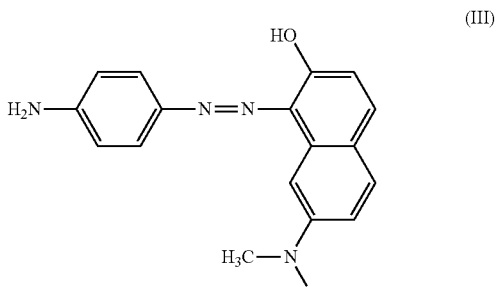

(III)

In the case of purifying a dye composition for hair dyeing which is positive in the Ames test in the present invention, it is preferable to perform the purification so that the content of the component contained in the purified dye composition for hair dyeing and represented by the structural formula (III) is 0.3 wt. % or less. The more preferable content is 0.25 wt. % or less, and the particularly preferable content is 0.2 wt. % or less.

The purification method for the dye composition for hair dyeing in the present invention is a method which was analyzed for the purpose of removing the component represented by the structural formula (III), and the purification method is characterized in that a dye composition for hair dyeing, which indicates positive in the Ames test, proves negative in the Ames test by performing the purification method.

The purification method for the dye composition for hair dyeing in the present invention is a method performed by treatment with activated carbon after dissolving the composition in a solvent. This treatment with activated carbon (adsorption purification) may be repeated.

A solvent used in the purification method for the dye composition for hair dyeing in the present invention need not be restricted if the objective dye composition for hair dyeing can be dissolved. However, it is particularly preferable to use a mixed solvent of water and a water-soluble organic solvent.

In the purification method for the dye composition for hair dyeing, the purification method of the present invention can be used in combination with a generally used purification method.

Examples of the purification method which can be used in combination with the purification method for the dye composition for hair dyeing in the present invention can be recrystallization, salting-out, activated carbon adsorption, column chromatography, and a sublimation purification method. These purification methods may be repeated and may be performed in combination with a different purification method.

The water-soluble organic solvent used in the purification method for the dye composition for hair dyeing in the present invention is not restricted. However, an aliphatic alcohol and an aliphatic ketone are preferable, and the aliphatic ketone is particularly preferable as the water-soluble organic solvent. As an aliphatic alcohol, it is preferable to use aliphatic alcohols of 1 to 5 carbon atoms such as methanol, ethanol, 1-propanol, 2-propanol, 1-butanol, isobutanol, tertiary butanol, and isoamyl alcohol, and it is particularly preferable to use an aliphatic alcohol of 3 to 4 carbon atoms. As an aliphatic ketone, it is preferable to use aliphatic ketones of 3 to 8 carbon atoms such as acetone, methyl ethyl ketone, methyl isopropyl ketone, methyl isobutyl ketone, diethyl ketone, ethyl isopropyl ketone, and ethyl isobutyl ketone, and it is more preferable to use an aliphatic ketone of 4 to 6 carbon atoms.

In the purification method for the dye composition for hair dyeing in the present invention, the mixing ratio (the volume ratio) between water and a water-soluble organic solvent is preferably 25/75 to 99.9/0.1, more preferably 40/60 to 80/20, and particularly preferably 50/50 to 70/30.

In the purification method for the dye composition for hair dyeing in the present invention, although a temperature when performing activated carbon adsorption depends on the boiling point of a used solvent, the temperature is preferably 20° C. to 100° C., more preferably 40° C. to 80° C., and particularly preferably 50° C. to 75° C.

In the purification method for the dye composition for hair dyeing in the present invention, the additive amount of the activated carbon is preferably 10 wt. % or more with respect to a dye composition for hair dyeing before purification. However, in the case where the content of the component contained in the dye composition for hair dyeing before purification and represented by the general formula (2) is less than 0.3 wt. %, the additive amount of the activated carbon may be decreased. It is preferable to repeat activated carbon adsorption until the content of the component represented by the general formula (2) becomes 0.3 wt. % or less.

In the purification method for the dye composition for hair dyeing in the present invention, a method for removing activated carbon after activated carbon adsorption, is not particularly restricted if it is a usually used method. However, it is preferable to use a method of filtration in view of convenience and facility of its treatment method on the site of producing industrial products.

In the purification method for the dye composition for hair dyeing in the present invention, a method for taking out a dye composition for hair dyeing from a solution after activated carbon adsorption, is not particularly restricted if it is a usually used method. However, it is preferable to use salting-out as a method for taking out the dye composition for hair dyeing in view of convenience and facility of its treatment method on the site of producing industrial products.

EXAMPLE 1

The following describes an embodiment of the present invention in more detail based on Examples. The present invention, however, is not restricted to the following Examples. Both of the purity and the content of the component represented by the structural formula (III) were determined by HPLC measurement. Basic Brown 16 in the following Examples means a dye composition for hair dyeing containing Basic Brown 16 as a main component.

139 kg of Basic Brown 16 produced by a publicly known method (HPLC purity: 88.0%; content of component represented by the structural formula (III): 0.6%), 869 L of water, and 521 L of methyl ethyl ketone were added to a reaction vessel and dissolved by heating up to 65° C. 13.9 kg of activated carbon was added to the obtained solution, and the activated carbon was removed by filtration after stirring at 65° C. for 2 hours. After this operation was repeated twice, the obtained filtrate was heated up to 55° C., and 270 kg of sodium chloride was added to perform salting-out. After cooled to a room temperature and filtrated, the product was washed using 209 kg of 18% salt solution and dried to obtain 100 kg of a purified product (yield: 72%). The HPLC purity of the purified product was 97.8%, and the content of the component represented by the structural formula (III) was 0.23%.

EXAMPLE 2

With respect to Basic Brown 16 before and after purification, the Ames test was carried out using *Salmonella typh-imurium* TA98 strain and *Salmonella typhimurium* TA1537 strain with and without an enzyme for activating metabolism of drugs (S-9Mix) in each strain. Table 1 summarizes the result (MR value).

TABLE 1

|  | TA98 | | TA1537 | |
| --- | --- | --- | --- | --- |
|  | −S9 | +S9 | −S9 | +S9 |
| Before purification | 2.3 | 42.6 | 2.6 | 6.3 |
| After purification | 1.5 | 1.5 | 1.7 | 1.2 |
| Component of structural formula (III) | 0.9 | 53.0 | 1.2 | 10.5 |

EXAMPLE 3

The Ames test was carried out on the same condition also with respect to the component indicating positive in the Ames test and represented by the structural formula (III) among impurities contained in Basic Brown 16. Table 1 summarizes the result.

EXAMPLE 4

With respect to Basic Brown 16 after purification, the Ames test was carried out using *Salmonella typhimurium* TA100 strain, *Salmonella typhimurium* TA1535 strain, and *Escherichia coli* WP2 uvrA strain with and without an enzyme for activating metabolism of drugs (S-9Mix) in each strain. All of the results were negative.

As shown in Table 1, the dye composition for hair dyeing before purification indicated the result of positive in both of the tests using TA98 strain and TA1537 strain. However, the dye composition for hair dyeing after purification was proved to be negative in both of the cases. The component, which is contained as an impurity in the dye composition for hair dyeing before purification and represented by the structural formula (III), indicated positive in metabolic activation tests of TA98 strain and TA1537 strain, and it was proved that the dye composition for hair dyeing proving negative in the Ames test can be obtained by performing purification to decrease the content of the component represented by the structural formula (III) to 0.3 wt. % or less.

Industrial Applicability

According to an embodiment of the present invention, a dye composition for hair dyeing containing, as a main component, an azo dye indicating negative in the result of the Ames test and having high safety, can be provided by carrying out a convenient and easy purification operation especially on an industrial producing site without requiring a complicated operation.

What is claimed is:

1. A dye composition for hair dyeing comprising, as a main component, an azo dye having trimethylammonio,
wherein a content of a compound contained in the dye composition for hair dyeing and represented by the following general formula (2) is 0.3 wt. % or less,

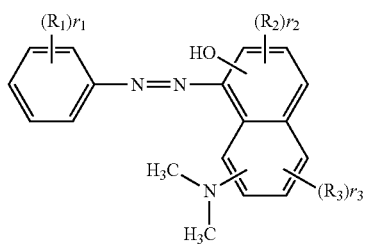

(2)

wherein $R_1$ to $R_3$ may be the same or different, and represent a hydrogen atom, nitro, amino, linear or branched alkyl of 1 to 10 carbon atoms that may have a substituent, cycloalkyl of 3 to 10 carbon atoms that may have a substituent, linear or branched alkyloxy of 1 to 10 carbon atoms that may have a substituent, cycloalkyloxy of 3 to 10 carbon atoms that may have a substituent, or a substituted or unsubstituted heterocyclic group; and $r_1$ is an integer of 0 to 5, $r_2$ is an integer of 0 to 2, and $r_3$ is an integer of 0 to 3, and wherein the result of the Ames test is negative.

2. The dye composition for hair dyeing according to claim 1, wherein the azo dye having trimethylammonio is represented by the following general formula (1):

[Chemical Formula 1]

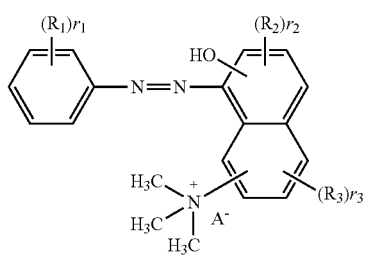

(1)

wherein $R_1$ to $R_3$ may be the same or different, and represent a hydrogen atom, nitro, amino, linear or branched alkyl of 1 to 10 carbon atoms that may have a substituent, cycloalkyl of 3 to 10 carbon atoms that may have a substituent, linear or branched alkyloxy of 1 to 10 carbon atoms that may have a substituent, cycloalkyloxy of 3 to 10 carbon atoms that may have a substituent, or a substituted or unsubstituted heterocyclic group; $r_1$ is an integer of 0 to 5, $r_2$ is an integer of 0 to 2, and $r_3$ is an integer of 0 to 3; and $A^-$ represents an anion.

3. The dye composition for hair dyeing according to claim 1, wherein the result of the Ames test using Salmonella typhimurium TA98 strain and/or Salmonella typhimurium TA1537 strain is negative.

4. The dye composition for hair dyeing according to claim 1, wherein the result of the Ames test using Escherichia coli WP2 uvrA strain is negative.

5. The dye composition for hair dyeing according to claim 1, wherein the azo dye having trimethylammonio is Basic Brown 16 represented by the following structural formula (I):

[Chemical Formula 3]

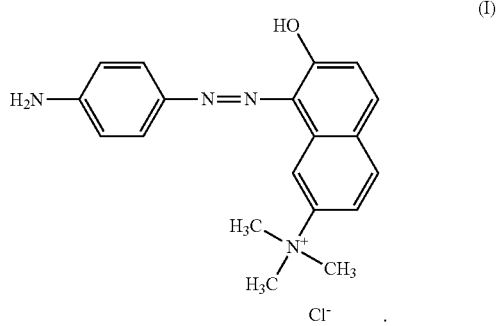

(I)

6. A purification method for a dye composition for hair dyeing containing, as a main component, an azo dye having trimethylammonio, wherein the purification is performed using activated carbon in a mixed solution of water and a water-soluble organic solvent, and wherein a result of the Ames test in the dye composition for hair dyeing is negative.

7. The purification method according to claim 6, wherein the azo dye having trimethylammonio is represented by the following general formula (1):

[Chemical Formula 4]

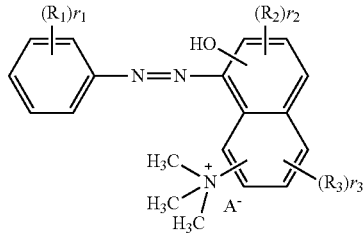

(1)

wherein $R_1$ to $R_3$ may be the same or different, and represent a hydrogen atom, nitro, amino, linear or branched alkyl of 1 to 10 carbon atoms that may have a substituent, cycloalkyl of 3 to 10 carbon atoms that may have a substituent, linear or branched alkyloxy of 1 to 10 carbon atoms that may have a substituent, cycloalkyloxy of 3 to 10 carbon atoms that may have a substituent, or a substituted or unsubstituted heterocyclic group; $r_1$ is an integer of 0 to 5, $r_2$ is an integer of 0 to 2, and $r_3$ is an integer of 0 to 3; and A represents an anion.

8. The purification method according to claim 6, wherein the result of the Ames test using Salmonella typhimurium TA98 strain and/or Salmonella typhimurium TA1537 strain is negative.

9. The purification method according to claim 6, wherein the water-soluble organic solvent is one or more selected from aliphatic alcohols and aliphatic ketones.

10. The purification method according to claim 6, wherein the content of the compound contained in the dye composition for hair dyeing and represented by the following general formula (2) is removed to 0.3 wt. % or less,

[Chemical Formula 5]

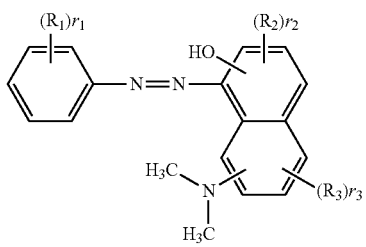

(2)

wherein $R_1$ to $R_3$ may be the same or different, and represent a hydrogen atom, nitro, amino, linear or branched alkyl of 1 to 10 carbon atoms that may have a substituent, cycloalkyl of 3 to 10 carbon atoms that may have a substituent, linear or branched alkyloxy of 1 to 10 carbon atoms that may have a substituent, cycloalkyloxy of 3 to 10 carbon atoms that may have a substituent, or a substituted or unsubstituted heterocyclic group; and $r_1$ is an integer of 0 to 5, $r_2$ is an integer of 0 to 2, and $r_3$ is an integer of 0 to 3.

11. The purification method according to claim 6, wherein the azo dye having trimethylammonio is Basic Brown 16 represented by the following structural formula (I):

[Chemical Formula 6]

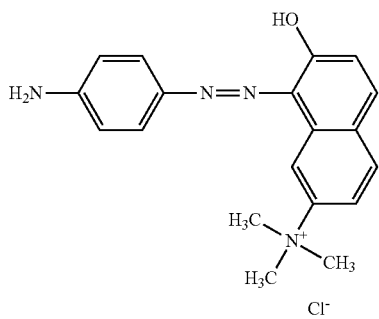

(I)

12. A producing method of a dye composition for hair dyeing containing, as a main component, an azo dye having trimethylammonio,
    wherein the method comprises a purification which is performed using activated carbon in a mixed solution of water and a water-soluble organic solvent, and
    wherein a result of the Ames test in the dye composition for hair dyeing is negative.

\* \* \* \* \*